(12) United States Patent
McInnes et al.

(10) Patent No.: US 8,230,862 B2
(45) Date of Patent: Jul. 31, 2012

(54) TRACHEAL TUBE SUPPORT APPARATUS

(76) Inventors: John Gordon McInnes, Kelowna (CA);
Aaron David Jackson, Kelowna (CA)

( * ) Notice: Subject to any disclaimer, the term of this patent is extended or adjusted under 35 U.S.C. 154(b) by 662 days.

(21) Appl. No.: 12/320,978

(22) Filed: Feb. 10, 2009

(65) Prior Publication Data

US 2010/0199997 A1     Aug. 12, 2010

(51) Int. Cl.
*A61M 16/00* (2006.01)
(52) U.S. Cl. .............................. 128/207.17; 128/207.11
(58) Field of Classification Search ............. 128/207.11, 128/207.14, 207.17
See application file for complete search history.

(56) References Cited

U.S. PATENT DOCUMENTS

| | | |
|---|---|---|
| 3,430,300 A | 3/1969 | Doan |
| 3,677,250 A | 7/1972 | Thomas |
| 3,927,676 A | 12/1975 | Schultz |
| 4,057,066 A | 11/1977 | Taylor |
| 4,074,397 A | 2/1978 | Rosin |
| 4,165,748 A | 8/1979 | Johnson |
| 4,460,356 A | 7/1984 | Moseley |
| 4,484,914 A | 11/1984 | Brown |
| 4,726,716 A | 2/1988 | McGuire |
| 4,822,342 A | 4/1989 | Brawner |
| 4,844,061 A | 7/1989 | Carroll |
| 5,038,778 A | 8/1991 | Lott |
| 5,135,506 A | 8/1992 | Gentelia et al. |
| 5,221,265 A | 6/1993 | List |
| 5,304,146 A | 4/1994 | Johnson et al. |
| 5,306,233 A | 4/1994 | Glover |
| 5,306,256 A | 4/1994 | Jose |
| 5,395,344 A | 3/1995 | Beisang, III et al. |
| 5,448,985 A | 9/1995 | Byrd |
| 5,468,231 A | 11/1995 | Newman et al. |
| 5,546,938 A | 8/1996 | McKenzie |
| 5,638,814 A | 6/1997 | Byrd |
| 5,743,885 A | 4/1998 | Hoerby |
| 5,797,394 A | 8/1998 | Boyd |
| 5,868,132 A * | 2/1999 | Winthrop et al. ........ 128/207.14 |
| 6,447,486 B1 | 9/2002 | Tollini |
| 6,866,652 B2 | 3/2005 | Bierman |
| 6,890,322 B2 | 5/2005 | Bertoch et al. |
| 7,231,921 B2 * | 6/2007 | Palmer .................... 128/207.17 |
| 2008/0173310 A1 | 7/2008 | Marcoe |
| 2009/0211573 A1 * | 8/2009 | Russo ..................... 128/200.26 |

* cited by examiner

*Primary Examiner* — Lynne Anderson
(74) *Attorney, Agent, or Firm* — Antony C. Edwards

(57) ABSTRACT

A flexible support for holding endotracheal and nasotracheal tubes in place on the face of a patient includes a pair of oppositely disposed adhesively mountable flanges for releasable mounting to the face of the patient, wherein the flanges are interconnected by a single narrow adhesive-backed elongate bridge-piece spanning between the opposite flanges, and wherein the bridge-piece is shaped so as to be mountable on either the filtrum or mandible of a patient, and wherein a pair of adhesive-backed wings are pivotally mounted by a flexible hinge to the bridge-piece for releasable adhesive mounting of the wings to a portion of the tracheal tube once intubated.

10 Claims, 5 Drawing Sheets

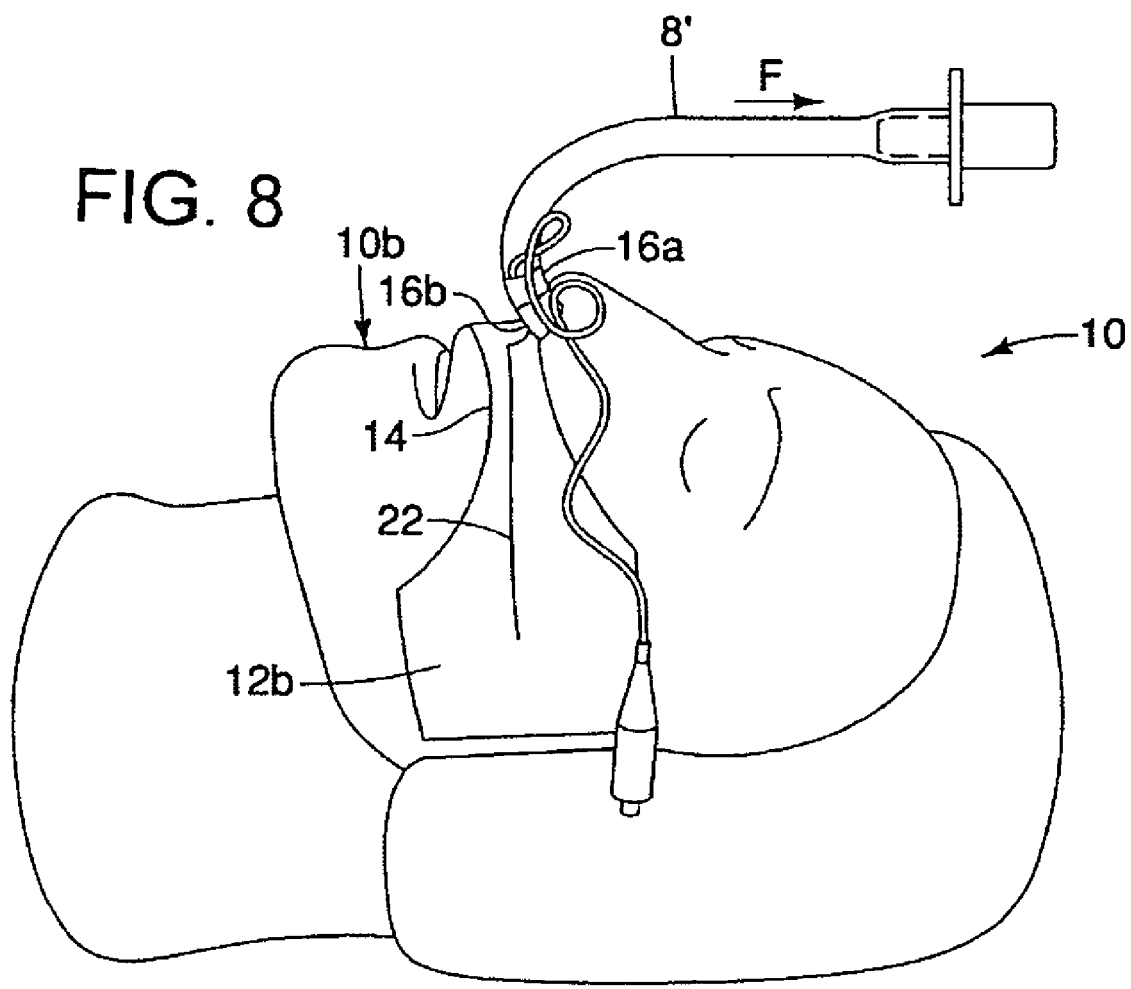

TRACHEAL TUBE SUPPORT APPARATUS

FIELD OF THE INVENTION

This invention relates to the field of supports for holding endotracheal and nasotracheal tubes in place on the face of a patient and in particular to a flexible support having a pair of oppositely disposed adhesively mountable plate-like flanges for releasable mounting to the cheeks of a patient, wherein the flanges are interconnected by a single narrow adhesive-backed elongate bridge-piece spanning contiguously between the opposite flanges, and wherein the bridge-piece is shaped so as to be mounted on either the filtrum or over the skin overlying the mandibular bone, hereinafter referred to as the mandible of a patient, and wherein a pair of adhesive-backed tenticle-like arms or wings are pivotally mounted to the bridge-piece for releasable adhesive mounting to a portion of the tracheal tube once the patient is intubated either orally or nasally.

BACKGROUND OF THE INVENTION

In the prior art applicants' are aware of U.S. Pat. No. 5,743,885 which issued to Hoerby on Apr. 28, 1998, for Bandage for Fixating an Oral Endo-Tracheal Anaesthesia Tube Relative to the Mouth of a Person and an Assembly for Fixating an Oral, Endo-Tracheal Anaesthesia Tube Relative to the Mouth of a Person. Hoerby discloses the use of a one or two part bandage to support an orally intubated endotracheal tube when the bandage is mounted on the face of a patient. In the one-part bandage embodiments, Hoerby teaches that both the filtrum and mandible of the patient are covered by an adhesively mounted bandage, where the bandage defines an aperture between the filtrum and mandible portions of the bandage. A further, mid-portion of the bandage is supported between the filtrum and mandible portions. The mid-portion is mountable to an endotracheal tube passed through the aperture. There is no teaching or suggestion by Hoerby to use a single fibre-reinforced bridging strip extending between wide plate-like flanges and supporting a centrally disposed pair of arms or wings from the bridging strip so that the bridging strip may be mounted either across the filtrum or across the mandible of a patient so as to allow mandibular or lower facial surgery or upper facial surgery respectively when the tracheal tube is inserted orally, or as to support the tracheal tube when intubated nasally.

In the prior art applicants are also aware of U.S. Pat. No. 5,038,778 which issued Aug. 13, 1991, to Lott for his Endotracheal Tube Tape. Lott discloses the use of a length of one sided adhesive tape having a central non-adhesive portion on the adhesive side of the tape for positioning under the neck of a patient. The opposite ends of the length of tape are brought from behind the neck up on either side of the patient's face and adhesively adhered. The ends of the length of tape are split to provide four strips of tape that are wrapped around the endotracheal tube to secure the tube in place. Other examples of the use of adhesive tape having a central non-adhesive portion and which is intended to wrap behind the neck of a patient and to secure an endotracheal tube to a patient's mouth are found in U.S. Pat. No. 5,306,233 to Glover and U.S. Pat. No. 5,797,394 to Boyd.

In the applicants view any endotracheal tube supporting device that encircles the neck of the patient is likely or prone to abrading the skin of the patient as the patient moves or is moved. Such a device is in applicants view an imperfect compromise between tensioning to avoid accidental and potentially life-threatening extubation and tensioning to avoid skin necrosis caused by decreased tissue perfusion. It is one object to provide anchoring skin fixation of a flexible tube support that does not encircle the neck and which provides minimal or no risk of pressure ischemia. It is a further object of the present invention to provide a support which incorporates an anatomical shape that balances a large surface area for adhesive anchoring on the face with the provision of only a narrow surface area over the filtrum or lower mandible. It is yet a further object to provide reinforcing fibres that inhibit the shearing effects of movement of an intubated tube pulling on the flexible support of the present invention to thereby prevent fracture and separation of the endotracheal tube from the support. Use of prior art multiple-piece supports only complicates the process of fixing the endotracheal tube to the patient and increases chances of incorrect placement and thus the potential failure of the support. The present invention is a one-piece application that is reversible so that it can be applied above or below the mouth to firmly affix the endotracheal tube in place after intubation, and which may be re-oriented by 180 degrees on the filtrum to provide for support of nasotracheal intubation. Use of prior art devices that adhere to the face and which surround the mouth are not appropriate for most types of oral or facial surgery. The support of the present invention may be releasably mounted on the mandible for upper face surgery and on the filtrum for mandible or lower facial surgery. It is yet a further object of the present invention to provide a support which fastens the endotracheal tube in the midline, permitting oral suctioning on both sides of the endotracheal tube and decreasing glottic trauma. Prior art devices which fix the endotracheal tube to one side of the patients mount apply irritating pressure on the patient's vocal cords.

SUMMARY OF THE INVENTION

In summary the flexible support for a tracheal tube intubated orally or nasally in a patient may be characterized as including first and second substantially planar flanges separated by, and joined contiguously to each other by, only a single elongate flexible bridge-piece. The bridge-piece is narrower than the flanges and is a unitary piece which is sized to releasably and conformally mount completely across either of the filtrum or the mandible of a human patient, but not both simultaneously. The bridge-piece is mountable across the filtrum to improve access for lower facial or mandible surgery and is mountable across the mandible to improve access for upper facial surgery. The bridge-piece is of only sufficient length so as to position the flanges onto the facial cheeks of the patient when the bridge-piece is mounted to the filtrum or mandible this allowing the flanges to adhesively anchor the bridge-piece.

A pair of flexible wings is mounted to the bridge-piece. Each wing has a basal end and an opposite free end. Each wing is mounted at its basal end to the bridge-piece substantially midway along the bridge-piece so as to be substantially centered on the filtrum or mandible of the patient when the bridge-piece is mounted thereon respectively. The pair of wings are deployable from a storage position adjacent to and co-planar with the bridge-piece when laid flat to an operational position substantially orthogonal to the bridge-piece. Once in the operational position the wings may be wrapped, for example helically, around an intubation tube positioned so as to bisect the oppositely disposed pair of wings, thereby adhesively attaching the tube to the bridge-piece.

The bridge-piece and the pair of wings may advantageously further include reinforcing such as fibres or strips or other flexible tensile resistive elongate members which extend along and continuously between the bridge-piece and the pair of wings.

The flange, the pair of wings when in their laid-flat storage position, the bridge-piece and the reinforcing are formed as a single sheet and are coplanar when the sheet is laid flat. Of the two opposite surfaces of the sheet, one side of the sheet has adhesive applied thereto for releasable mounting of the flanges to the facial cheeks of the patient, the bridge-piece to either the filtrum or mandible of the patient, and the pair of wings to the tracheal tube when intubated either orally or nasally in the patient. As used herein, reference to tracheal tube or endotracheal tube or intubating tube is intended to collectively refer to both endotracheal and nasotracheal tubes. Further, although not its primary purpose, the tracheal tube according to the present invention may also be used to hold an oral/naso gastric tube in place while holding the endotracheal tube.

The flanges have a sufficient surface area so that the flanges remain anchored by the adhesive to the facial cheeks of the patient when the wings are wrapped around so as to support the endotracheal tube. In one preferred embodiment the planform outline of the support is dumb-bell shaped so that the narrow bridge-piece inter-connecting the two opposite and wider flanges has a width that is narrower than the width of the flanges by a ratio of substantially at least four times wider than the width of the bridge-piece. This allows for the secure anchoring of the flanges while using a relatively easily removable adhesive which may be peeled off the skin of the patient for example by pulling a non-adhesively backed tab provided on the opposite end edges of the flanges, with minimal disruption to the surgical area if on the face of the patient.

Advantageously the supports may be formed from a rectangular blank of flexible material such as one-sided adhesive tape which may be pre-formed in the rectangular blank so that upon use the wings may be separated from their adjacent bridge-piece, with the exception of a hinge portion connecting the wings to the bridge-piece. On the side opposite to the wings, a cut-out portion may be detached from the rectangular blank leaving the waisted centrally extending remaining strip as the bridge-piece. The blank may be provided with pre-cut outlines formed therein so that the end user merely has to separate the wings and the cut-out from the opposite sides of the bridge-piece to produce the useful endotracheal tube support according to the present invention, or these separations may be done at a manufacturing facility prior to shipping of the supports for distribution to the end-users. In the former instance, the pre-cut blanks may be provided in roll form as a serial end-to-end continuous strip of such blanks which may be pulled from the roll and separated along perforated dividing lines for use when and as needed.

BRIEF DESCRIPTION OF THE DRAWINGS

FIG. 8 is, in side elevation view, an embodiment of the flexible support having wider anchoring flanges than the embodiments of FIGS. 1*a* and 1*b*, and mounted with the bridge of the support over the filtrum of the patient so as to support a nasally intubated tracheal tube.

DETAILED DESCRIPTION OF EMBODIMENTS OF THE INVENTION

Figure 1A:
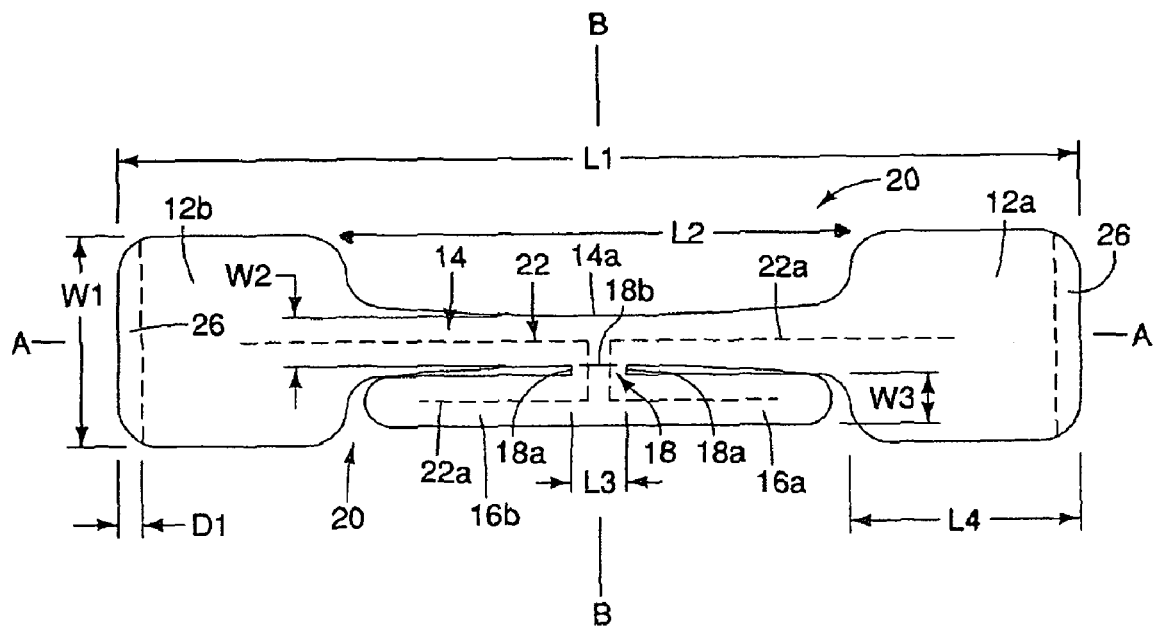
FIG. 1*a* is, in plan view, one embodiment of the flexible support for an endotracheal tube according to the present invention.
Figure 1B:
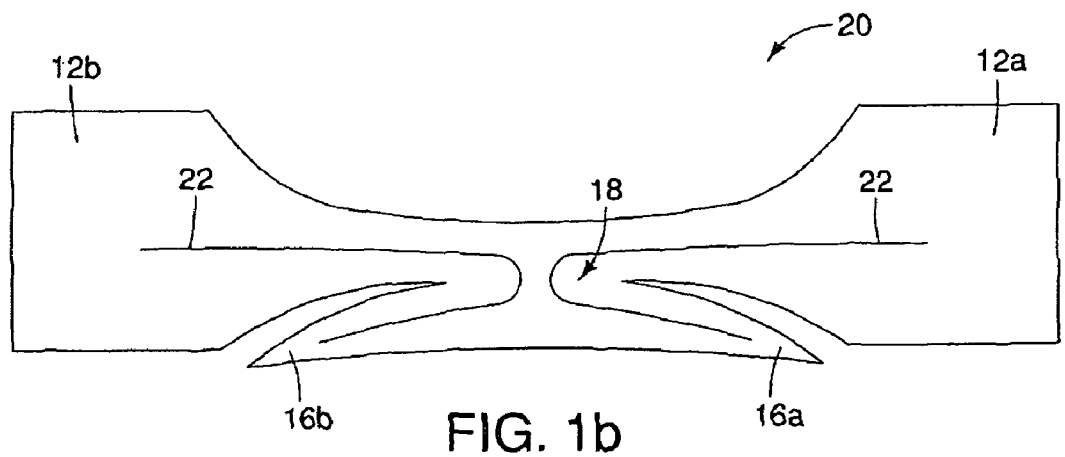
FIG. 1*b* is, in plan view, an alternative embodiment of the flexible support of FIG. 1*a*.

As seen in FIGS. 1*a* and 1*b* the flexible support for a tracheal tube may in one embodiment be a planar sheet having adhesive on only one side, and shaped in the form of a double-ended paddle or dumb-bells when viewed in plan view. A pair of arms or wings (herein collectively referred to as wings) are mounted midway along the narrow portion of the paddle-shape. The opposite ends of the paddle-shape provide each end with wide planar flanges 12*a* and 12*b* respectively, joined together by a much narrower flexible band or bridge-piece 14. The wings are a pair of oppositely disposed wings 16*a* and 16*b* mounted centered along the length of bridge-piece 14 by a flexible connecting hinge 18. Wings 16*a* and 16*b* may have smoothly rounded ends such as shown in FIG. 1*a* or may have more sharply pointed ends such as seen in figure 1*b*, or may otherwise have squarely truncated or other shaped ends so long as the length of the wings are sufficient to securely wrap the adhesive side thereof around a tracheal tube as better described below.

Bridge-piece 14 is sufficiently long and sufficiently narrow so that bridge-piece 14 may be secured over alternatively either the filtrum 10*a* or the mandible 10*b* of patient 10 and so that flanges 12*a* and 12*b* may be secured with their adhesive side flush against the cheeks or jaw of the patient. In one embodiment, which is useful for forming the endotracheal tube support according to the present invention from a roll of flexible adhesive backed material such as fabric in the manner of a roll of single-sided adhesive fabric tape, the bridge-piece 14 is formed along a longitudinally medial axis A between a pair of substantially mirror image oppositely disposed cut-outs 20. Wings 16*a* and 16*b* mounted on hinge 18 are formed within one of the cut-outs 20.

The placement of bridge-piece 14 centred along axis A between flanges 12*a* and 12*b*, although not intended to be limiting, is advantageous in that tension applied to bridge-piece 14 will be evenly distributed to flanges 12*a* and 12*b* so as to evenly resist the peeling or shearing of the flanges from where they are adhesively secured to the cheeks or jaw of the patient. The tension load on bridge-piece 14 results from the securing of wings 16*a* and 16*b* about endotracheal tube 8 when the endotracheal tube is intubated in patient 10. Wings 16a and 16b transfer the tensile loading resisting movement of endotracheal tube 8 and thereby transfer the tensile loading via binge 18 to bridge-piece 14.

As the endotracheal tube 8 may not necessarily cause a tensile loading which is centred between flanges 12a and 12b. That is, due to movement of tube 8 the tensile loading may not be necessarily only in a plane containing lateral axis B and which is orthogonal to the plane containing the sheet of the endotracheal tube support when laid flat. For example, if the endotracheal tube while intubated is inadvertently bumped or pulled to one side of the patient, then the tension applied to hinge 18 will be to one side or the other of axis B causing stress concentrations at the side edges 18a of hinge 18 tending thereby to shear across the hinge. The shearing of the hinge is resisted by for example rounding of the side walls along side edges 18a or for example by widening or thickening hinge 18. In a preferred embodiment the use of fibre reinforcing 22 (shown in dotted outline in FIG. 1a) assists resisting shearing and the ultimate fracturing and thus separating the wings from the bridge-piece. Fibre reinforcing 22 is intended to include the use of single or multiple strands of elongate tensile resistive fibres, strands or strips (collectively referred to herein as fibres) which, in a preferred embodiment, extend the length of bridge-piece 14, and which also extend across hinge 18 and along substantially the length of wings 16a and 16b. Thus is seen in FIG. 1a, fibre reinforcing 22 may be comprised of a pair of fibres 22a where each is U-shaped. The U-shaped fibres bridge hinge 18 and are oppositely disposed. In particular, the adjacent base of each U-shaped fibre bridges hinge 18 so as to provide a double reinforcement of the hinge to resist a shear or tear or fracture of the hinge.

Figure 2:
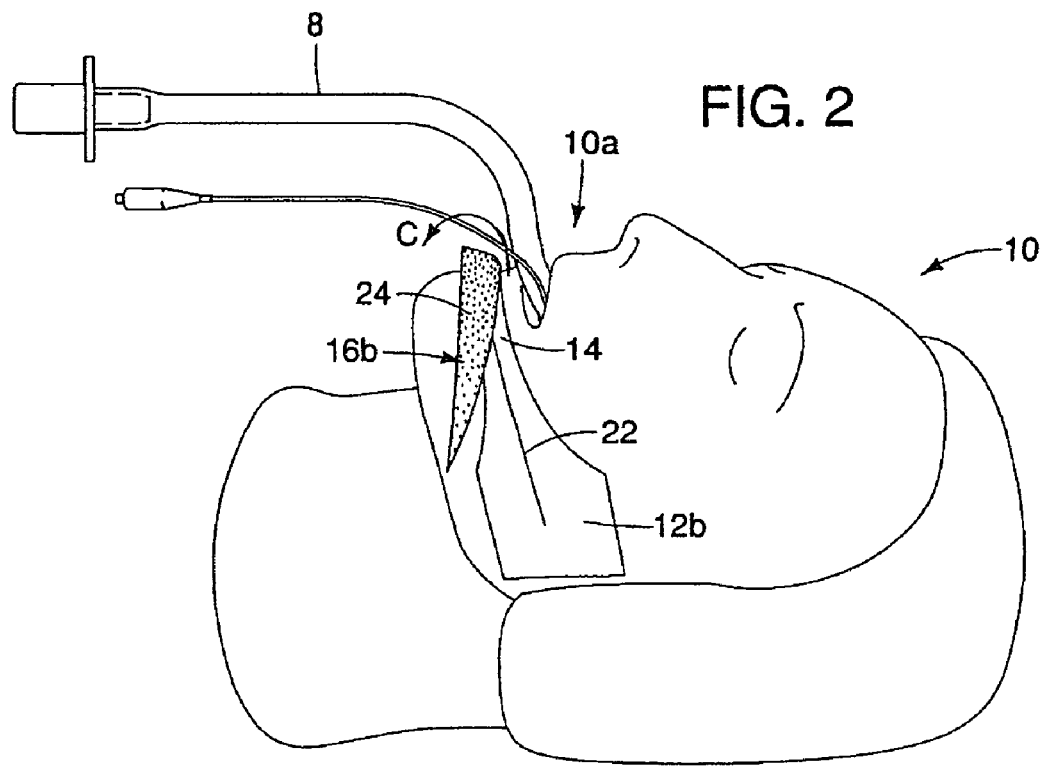
FIG. 2 is, in side elevation view, the flexible support of FIG. 1*b* mounted over the lower mandible of a patient orally intubated with an endotracheal tube. The oppositely disposed pair of flexible adhesive wings have been deployed from their storage position adjacent the bridge of the support to their operative position ready for adhesively wrapping onto the endotracheal tube.

The use of a flexible hinge 18 allows the wings 16a and 16b to be folded upwardly in direction C as seen in FIG. 2 out of their storage position flush along and co-planar with bridge-piece 14 when laid flat. Thus, in use, once flanges 12a and 12b have been adhesively mounted to the opposite sides of the patient's face, either to the jaw area when bridge-piece is mounted across the patient's mandible 10b, or the cheeks of the patient when the bridge-piece 14 is mounted to the filtrum 10a of the patient, hinge 18 is then bent through typically approximately 90 degrees as wings 16a and 16b are folded over in direction C about hinge 18. This exposes the adhesive side of the wings away from the patient's face. In FIG. 2 the adhesive surface of the wings is indicated by reference numeral 24. It is understood that in a preferred embodiment, the entire underside surface of flanges 12a and 12b, bridge-piece 14, hinge 18, and wings 16a and 16b would be coated in a releasable adhesive of a kind known to those skilled in the art which releasably adheres to human skin and which adheres to an endotracheal or nasotracheal tube with sufficient adherence to retain same in place.

Figure 3:
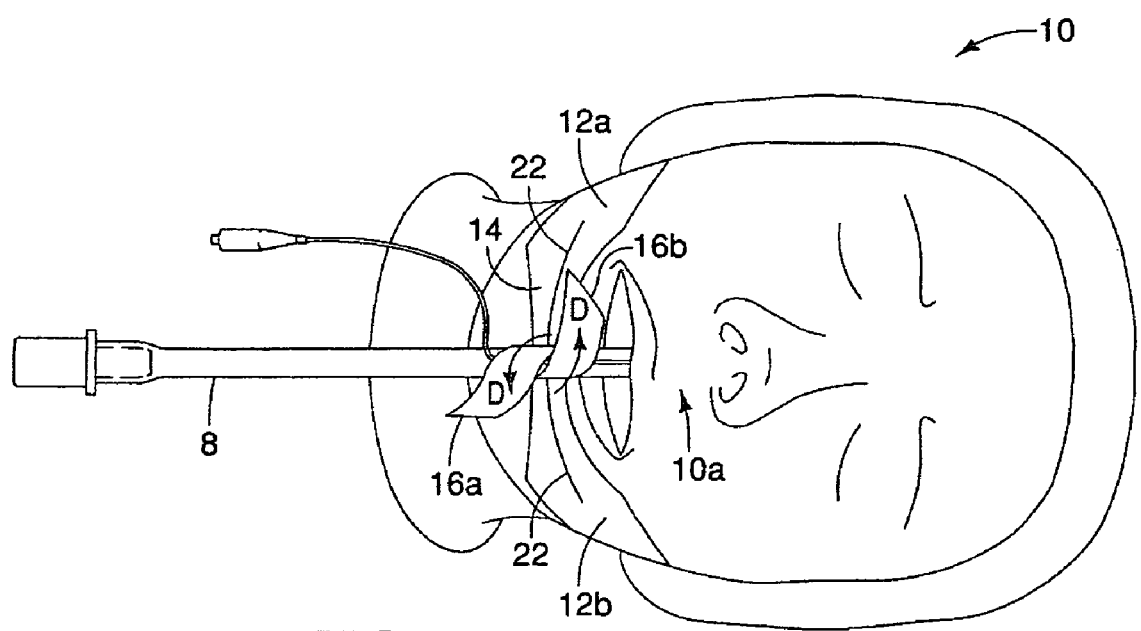
FIG. 3 is, in plan view, the flexible support as mounted on the patient of FIG. 2 illustrating the flexible wings being helically wrapped onto the endotracheal tube so as to be releasably adhesively mounted thereto.
Figure 4:
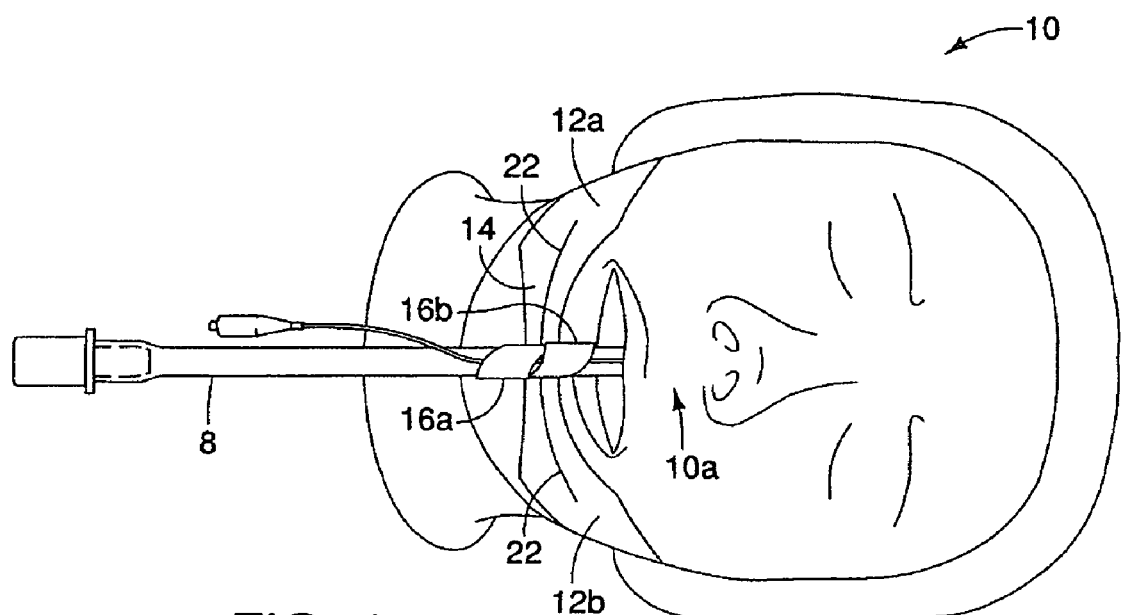
FIG. 4 is the view of FIG. 3 illustrating the flexible wings of the support having been completely helically wrapped onto the endotracheal tube so as to support the endotracheal tube anchored to the lower mandible and lower cheeks of the patient.
Figure 5:
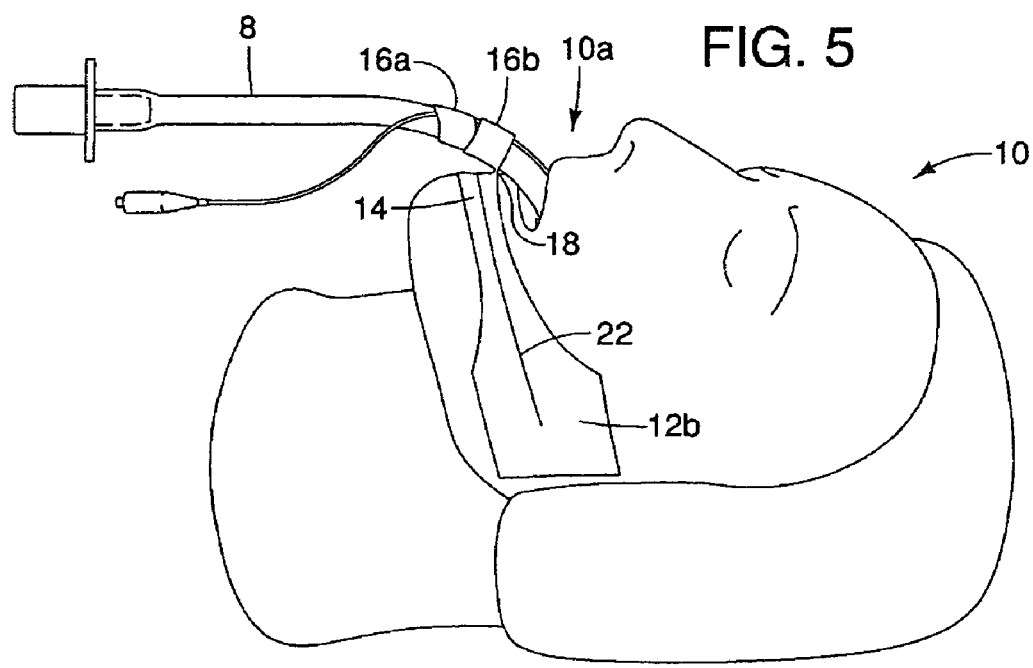
FIG. 5 is, in side elevation view, the flexible support as mounted on the patient of FIG. 4.

Thus with hinge 18 folded about hinge line 18b so as to fold the wings 16a and 16b into their operative position folded over approximately 90 degrees, that is, so as be typically substantially orthogonal to the centre portion 14a of bridge-piece 14 as seen for example in FIG. 2, and with endotracheal tube 8 intubated, wings 16a and 16b are then wrapped helically in opposite directions D about the portion of endotracheal tube 8 adjacent the intubation site. This wraps adhesive 24 into contact with the outer wall of the endotracheal tube. The wings are wrapped helically about the endotracheal tube in counter directions to one another as seen in FIG. 3. Wings 16a and 16b are wrapped until entirely flush mounted around endotracheal tube 8 as seen in FIGS. 4 and 5. With endotracheal tube 8 now supported by reason of the support anchoring the tube to the patient's mandible, a surgical procedure, for example to the upper facial area of the patient, may proceed with minimal risk of extubation of the endotracheal tube.

Figure 6:
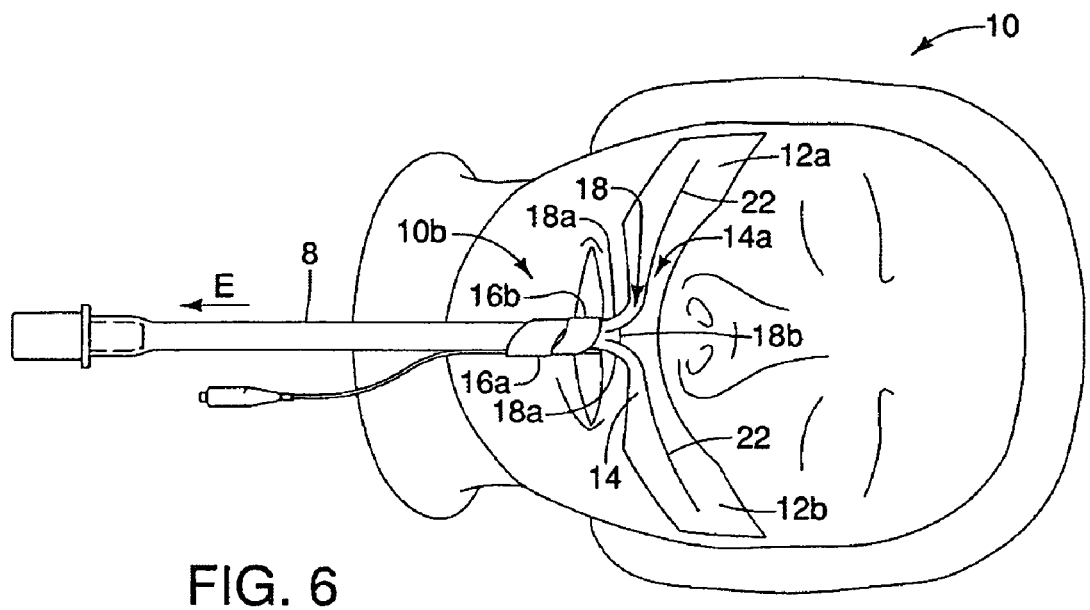
FIG. 6 is, in plan view, the flexible support of FIG. 1*b* mounted across the filtrum of the patient and anchored to the upper cheeks of the patient so as to support an orally intubated endotracheal tube by means of the wings mounted to the bridge of support being adhesively helically wrapped onto the endotracheal tube.
Figure 7:
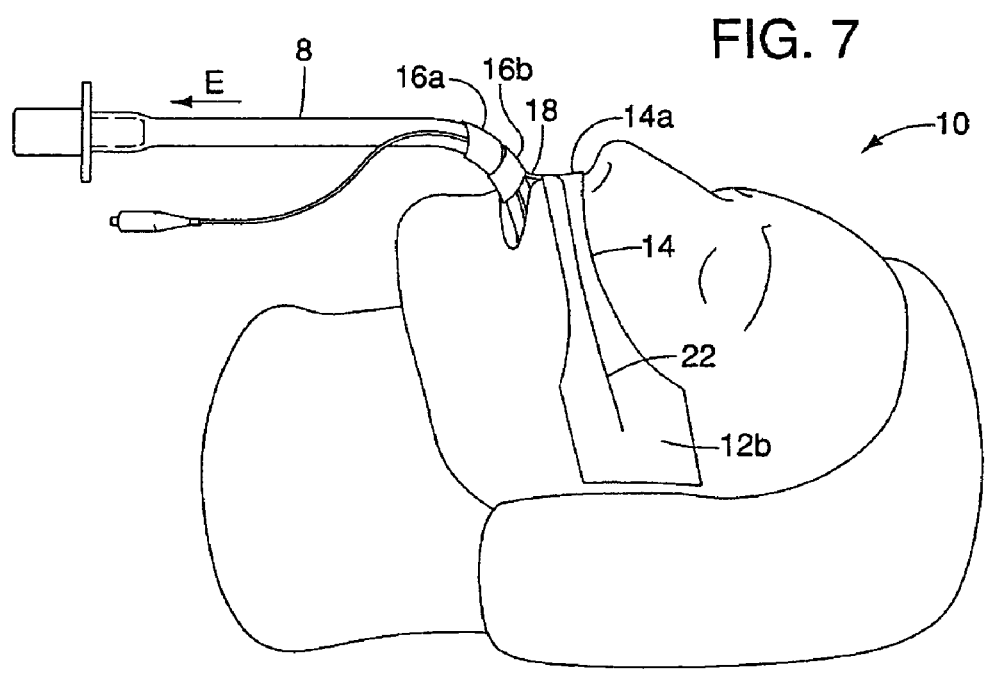
FIG. 7 is, in side elevation view, the flexible support as mounted on the patient of FIG. 6.

As seen in FIGS. 6 and 7, the endotracheal tube support according to the present invention may also be mounted across filtrum 10a so as to allow surgical access to the patient's mandible or lower facial area 10b. Whereas in the application of the support to the mandible the flanges 12a and 12b were mounted to the patients lower cheek or jaw region, in the application of FIGS. 6 and 7, the flanges 12a and 12b are mounted to the mid-to-upper cheeks of the patient so as to provide tensile support to bridge-piece 14 which has been adhesively mounted across filtrum 10a. In the example illustrated, because endotracheal tube 8 has been deflected so as to extend from the patient's mouth down along the patient's neck, hinge 18, although initially folded to approximately 90 degrees from mid-portion 14a of bridge-piece 14, and because wings 16a and 16b are helically wrapped to follow along endotracheal tube 8, the folded inclination of hinge 18 is relaxed so as to form an obtuse angle relative to mid-portion 14a although, as the term substantially orthogonal is intended to be used herein, still remaining substantially orthogonal relative mid-portion 14a of bridge-piece 14. Thus a tensile loading pulling on endotracheal tube 8 in direction E transfers a corresponding tensile loading via wings 16a and 16b and hinge 18 to bridge-piece 14. The tensile loading is transferred to the face of the patient by means of bridge-piece 14 and also via flanges 12a and 12b as the tensile loading is transferred along the flexible and preferably porous material of the support and fibres 22.

As seen in FIG. 8, the tracheal tube support according to the present invention may also be used where the patient is intubated nasally with nasotracheal tube 8'. For this application, the support is oriented as described above for use of endotracheal tubes in association with intubating the patient orally using the support mounted to the mandible of the patient. That is, the support is oriented with wings 16a and 16b on the side of bridge-piece 14 towards the upper facial area of the patient. The difference between the use of the support as described in relation to FIGS. 2-5 is that in the use illustrated in FIG. 8 nasotracheal tube 8' is intubated nasally and, as shown, in this example the tracheal tube is deflected away from the intubation site so as to extend over the patient's forehead. The tension in this instance then is in direction F which, again, is transferred as a tensile force through wings 16a and 16b, hinge 18 and bridge-piece 14 via the flexible material and reinforcing fibre 22 to the adhesive anchoring provided by flanges 12a and 12b mounted onto the patient's cheeks. As also illustrated in FIG. 8, flanges 12a and 12b may in some embodiments be relatively large and plate-like so as to cover a substantial portion of the patient's cheeks when mounted thereon. In this fashion, a lighter adhesive, that is, a less adhesively retentive adhesive may be employed as adhesive 24. The use of a lighter adhesive may minimize the difficulty in removing the support from the patient after use. Minimizing the adhesive force with which the support is glued to the patient's cheeks reduces the risk of trauma to an adjacent surgical area when the support is peeled from the face of the patient.

In order to assist in removal of the support from the patient's face, in a preferred embodiment, as seen in FIG. 1a, non-adhered tabs 26 are formed at the opposite ends of support by leaving the underside of flanges 12a and 12b underneath tabs 26 free of any adhesive 24. Thus, when the support is otherwise adhesively mounted onto the face of the patient, the distal edges of the flanges may be lifted by lifting non-adhered tabs 26 and gently thereafter pulling upwardly to release the adhesive.

In a further alternative embodiment, the adhesive applied under wings 16a and 16b is an adhesive which is different than that applied under the flanges 12a and 12b and under bridge-piece 14. For example the adhesive used to adhere the wings may be adapted to adhere more strongly to the walls of the tracheal tube than the level of adhesion used to adhere the flanges to the patient's face.

With reference again to the support illustrated by way of example in FIG. 1a, in that embodiment, and without intending to be limiting, the dimensions may be substantially as follows (expressed in centimeters): W1 (the width of the support) is 4.7 cm, W2 (the width of the tapered mid-portion 14a of bridge-piece 14) is 1.2 cm, W3 (the width of the wings) is 1.2 cm, length L1 (the overall length of the support) is 21.0 cm, length L2 (the length of the cut-outs 20) is 11.0 cm, the length L3 (the length of hinge line 18b) is 1.2 cm, the length L4 of each flange is 5.0 cm, and the depth D1 of each pull tab 26 is 0.5 cm.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A flexible support for an endotracheal tube intubated orally or nasally in a patient, the support comprising:

a single flexible unitary sheet having a pair of flanges, a bridge-piece connecting said pair of flanges and a pair of wings hingedly mounted to said bridge-piece, said pair of flanges separated by, and joined contiguously to each other by, only said bridge-piece, wherein said bridge-piece is narrower than said pair of flanges and has a longitudinal axis extending along said bridge piece from and between said pair of flanges, wherein said bridge-piece is unitary and sized to releasably and conformally mount completely across either of a filtrum, a mandible of a human patient, but not both simultaneously, so that said bridge-piece is mountable across the filtrum for lower facial or mandible surgery and across the mandible for upper facial surgery, and where said bridge-piece is of only sufficient length so as to position said pair of flanges onto the facial cheeks of the patient when said bridge-piece is so mounted, said pair of wings oppositely disposed, each wing of said pair of wings having a basal end and an opposite free end, a hinge said hingedly connecting said basal ends of said pair of wings to said bridge piece, wherein said hinge has a corresponding hinge axis which is substantially parallel to said longitudinal axis of said bridge-piece, wherein each said wing is flexible and mounted at its corresponding said basal end to said hinge and said hinge mounted to said bridge piece substantially midway along said bridge piece so as to be substantially centered on the filtrum or mandible of the patient when said bridge-piece is mounted thereon respectively, said pair of wings deployable about said hinge axis of said hinge from a storage position adjacent to and substantially co-planar with said bridge-piece when laid flat to an operational position substantially orthogonal to said bridge-piece by pivoting said basal ends of said pair of wings about said hinge axis, wherein said pair of flanges, said pair of wings when in said storage position, said hinge, and said bridge-piece are formed as a single sheet having two opposite surfaces and are coplanar when said sheet is laid flat, and wherein, of said two opposite surfaces of said sheet, only a lower side of said sheet has adhesive applied thereto for releasable mounting of said pair of flanges to the face of the patient and said bridge-piece to either the filtrum or mandible of the patient, and for releasable mounting of said pair of wings to an endo-tracheal tube intubated or to be intubated either orally or nasally in the patient when said pair of wings are in said operational position, and wherein said flanges are of sufficient surface area so that said flanges remain anchored by said adhesive to the cheeks of the patient when said pair of wings is in said operational position and supporting the endo-tracheal tube.

2. The support of claim 1 wherein platform outline when laid flat, said flanges and said bridge-piece provide a substantially dumbbell shape.

3. The support of claim 2 wherein said flanges have a first width and said bridge-piece has a second width, and wherein the ration of said first width to said second width is substantially at least 4:1.

4. The support of claim 1 wherein said bridge-piece is formed between a cutout-portion on a first lateral side of said bridge-piece and said pair of wings on a second lateral side of said bridge-piece opposite said first lateral side.

5. The support of claim 4 wherein said flanges, said bridge-piece, said pair of wings and said cut-out portion define substantially a rectangle.

6. The support of claim 1 wherein said bridge-piece and said pair of wings further comprises flexible reinforcing extending across said hinge and along and continuously between said bridge-piece and said pair of wings.

7. The support of claim 6 wherein said hinge is substantially centrally disposed between said pair of wing.

8. The support of claim 7 wherein said pair of wings are separated from said bridge-piece by a corresponding pair of separating cut-lines having an adjacent terminus and wherein said hinge is located between said adjacent terminus of each of said pair of separating cut-lines.

9. The support of claim 8 wherein said hinge axis is substantially co-linear with an adjacent edge of said bridge-piece and wherein said pair of wings in said operational position are deformable to counter-rotatively wrap around a tracheal tube positioned across said hinge axis so as to bisect said pair of wings in centrally disposed alignment with said hinge.

10. The support of claim 9 wherein said wings are shaped to allow for helical wrapping in opposite directions relative to one another about the tracheal tube.

* * * * *